United States Patent [19]

Trod

[11] 4,309,384
[45] Jan. 5, 1982

[54] CHEMICAL ANALYSIS CUVETTE

[76] Inventor: Ernest Trod, 2376 Roosevelt Cir., Santa Clara, Calif. 95051

[21] Appl. No.: 137,503

[22] Filed: Apr. 4, 1980

[51] Int. Cl.³ .................... G01N 35/02; G01N 21/07
[52] U.S. Cl. ................................. 422/64; 356/246; 422/72
[58] Field of Search ................... 422/72, 64, 102; 356/246

[56] References Cited

U.S. PATENT DOCUMENTS

| 3,681,029 | 8/1972 | Shapiro | 422/72 X |
| 3,801,283 | 4/1974 | Shapiro et al. | 422/72 X |
| 4,225,558 | 9/1980 | Peterson et al. | 422/72 |

Primary Examiner—Ronald Serwin
Attorney, Agent, or Firm—Richard Alan Brown

[57] ABSTRACT

In a photometric solution analyzer of the rotary type wherein a carousel includes a multiplicity of improved cuvettes, the carousel being journaled on a shaft driven by a motor, the analyzer further including means for permitting transfer of radiant energy from a source thereof to a detector therefor along an optical path passing through at least part of each of the cuvettes, the cuvettes being disposed about the carousel for receiving and mixing a reagent and a sample, each improved cuvette comprising a sample holding means being disposed in each cuvette for receiving the sample, the sample holding means being located radially outward from the center of the carousel, and a chamber being disposed for receiving the reagent, the chamber being located below the sample holding means and radially inward of the sample holding means, the chamber further being disposed in the optical path so that radiant energy is passed therethrough, whereby rotation of the carousel causes the reagent in each cuvette to flow towards the sample holding means to effect mixture of the reagent with the sample.

7 Claims, 4 Drawing Figures

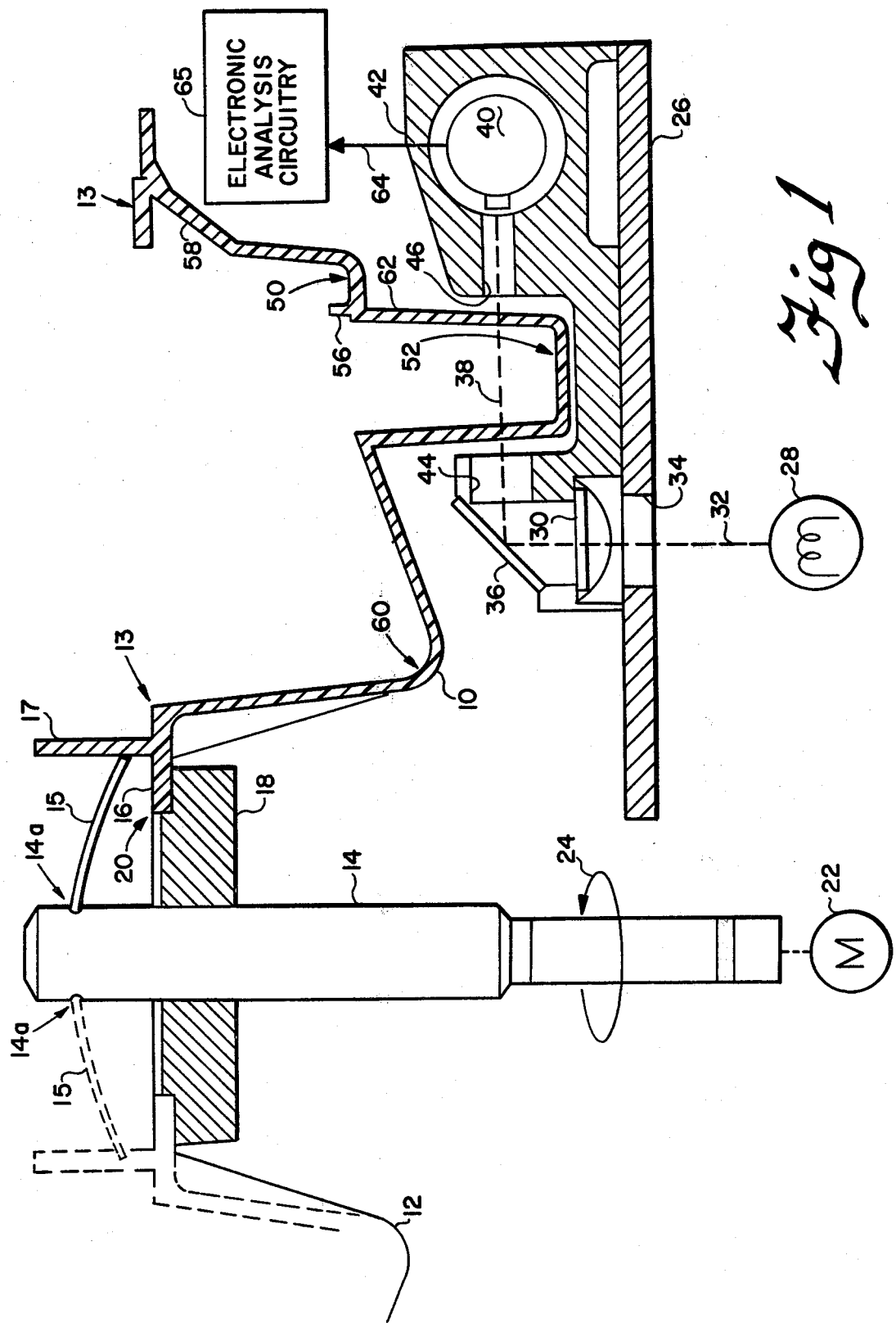

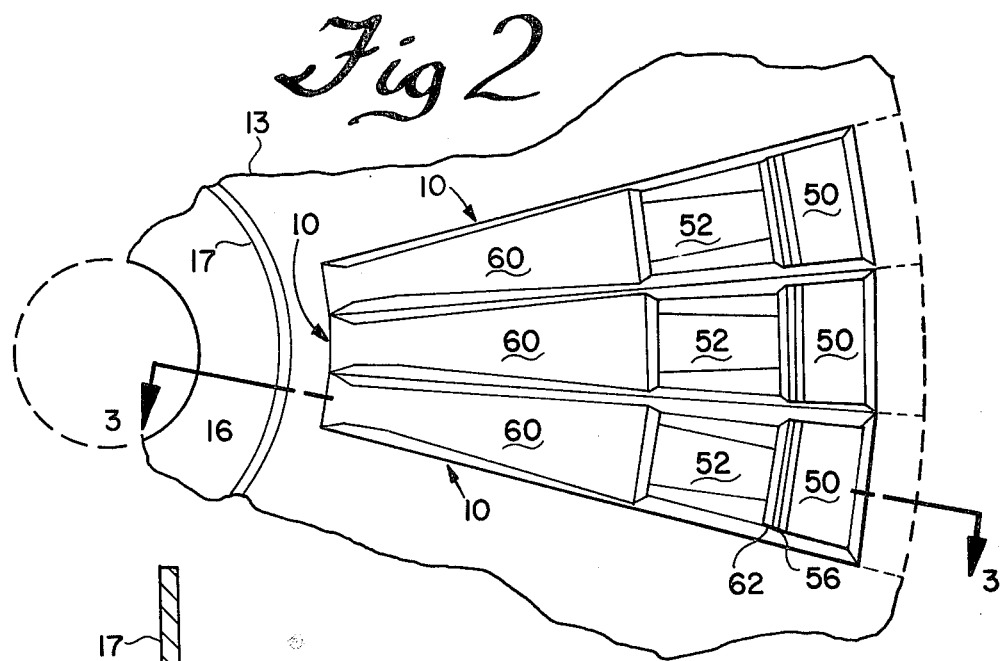
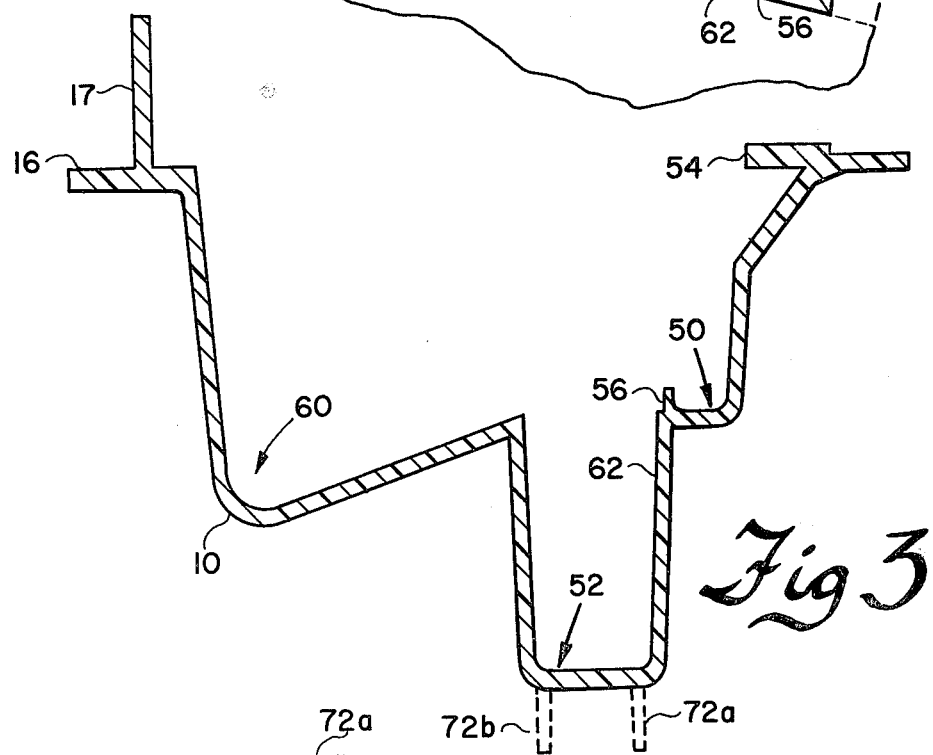
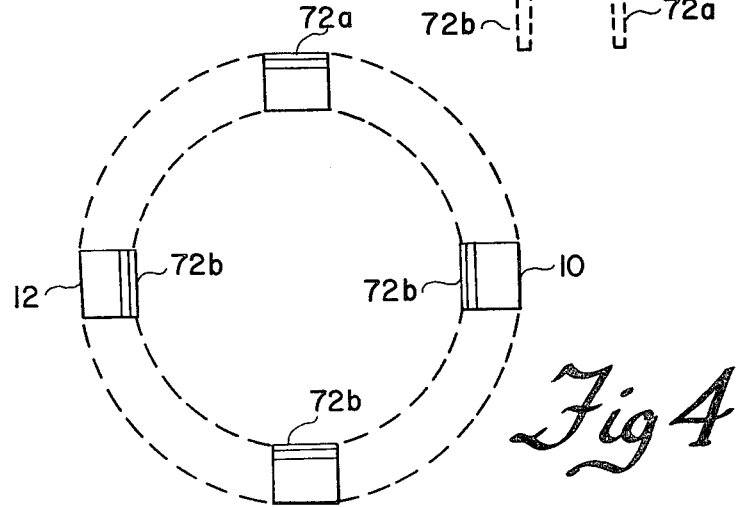

CHEMICAL ANALYSIS CUVETTE

BACKGROUND OF THE INVENTION

This invention relates to a new and improved chemical analysis photometer, and more particularly to such a photometer having an improved cuvette structure that provides for a zero reading of the reagent prior to mixture of a reagent and a sample.

The term "photometric" as used herein should not be considered in a restrictive sense as it is intended to be generic to the terms "colorimetric", "fluorometric" and "spectrometric". Also, the term "photometer" as used herein should not be considered in a restrictive sense and includes but is not limited to those devices sometimes referred to in the art as "colorimeters", "fluorometers" and "spectrometers". The term "light" as used herein includes radiant energy in both the visible and invisible spectrums as well as radiant energy restricted to specific wave lengths. Thus, this invention should be understood to encompass systems which utilize different types of radiation to accomplish the measurement desired. The terms "above", "below", "inward" and "outward" are used herein when viewing the drawings in a conventional manner.

An example of a prior art photometer is described and illustrated in U.S. Pat. No. 3,555,284, entitled "Multistation, Single Station Channel Analytical Photometer and Method of Use." In particular, this patent teaches a photometer that passes light through a reaction or mixing chamber which is disposed radially from separate reagent and sample chambers. Upon rotation, the sample and the reagent move under centrifical force to the reaction chamber whereupon light is passed through the reaction chamber to obtain a reading. Since the reagent and sample are mixed either before or simultaneously with the light reading, there is no way to obtain a reagent blank reading or a zero reading as the term is sometimes used herein. Thus, a reagent blank reading must be assumed. The term "obtain a reading" as used herein refers to the measurement of light transmitted through a solution in the reaction chamber of the cuvette. More particularly and as a general rule, a spectrophotometric measurement is made of the light that passes through the solution in the reaction chamber. However, light readings can be taken throughout the electromagnetic spectrum. The term "light reading" herein refers to the measurement of electromagnetic energy transmitted through the solution.

Another prior art photometer is described and illustrated in U.S. Pat. No. 3,586,484 entitled "Multistation Analytical Photometer and Method of Use." The structure of this invention is substantially the same as that of the '284 patent above. The reagent and sample are both initially placed in separate chambers, and upon rotation they mix in a third chamber. The resulting mixture is passed through a series of passageways and intermediate chambers before being deposited in a sampling chamber for analysis by light rays. Thus, there is no means of obtaining a reagent blank reading and one must be assumed. Also, it is necessary to either calibrate each cuvette to each other or to a reference because of the potential difference of the walls of each cuvette in transmitting light or to take readings to compensate for the optical transmitting difference between each cuvette, or to manufacture each cuvette so that the optical transmitting characteristic of all cuvettes is equal. U.S. Pat. No. 3,681,029 entitled "Sample Holder and Transferring Device for a Centrifuge" is very similar to the photometer of the '284 patent, and has the same disadvantage.

Yet another prior art device is described and illustrated in U.S. Pat. No. 3,873,217 entitled "Simplified Rotor for Fast Analyzer of Rotary Cuvette Type." The apparatus of this patent includes inner reagent chambers and outer sample chambers. Upon rotation, the reagent is moved to the outer sample chamber by centrifical force for mixture thereof. The light rays are passed through the sample or mixture chambers for analysis. Accordingly, it may be appreciated that a reagent blank reading may not be obtained, but must again be assumed, because the sample and not the reagent is placed in the reaction chamber and this patent has the additional disadvantage noted above for the '284 patent.

A more recent prior art apparatus is described in U.S. Pat. No. 3,811,780 entitled "Chemical Analysis Cuvette." This apparatus is capable of allowing for a reagent blank reading since the light rays are passed through the reaction chamber containing the reagent prior to mixture with a sample. However, this is a complicated apparatus, and as designed does not use centrifical force of the carousel for mixing but instead for stepping from one chamber to the next such that a syringe may be employed for transferring the sample (backed by the reagent) into a reaction chamber. Thus, as designed, this apparatus also mixes the reagent and the sample before the light rays are passed through the reaction chamber for analysis. Accordingly, a reagent blank reading must again be assumed and this patent has the additional disadvantage as noted above for the '284 patent.

Furthermore, the prior art systems require the use of a reagent blank solution separate from the test solution to obtain blank reading. Thus, at least two aliquots of reagent are required.

SUMMARY OF THE INVENTION

In a photometric solution analyzer of the rotary type wherein a carousel includes a multiplicity of improved cuvettes, the carousel being journaled on a shaft driven by a motor, the analyzer further including means for permitting transfer of radiant energy from a source thereof to a detector therefor along an optical path passing through at least a part of each of the cuvettes, the cuvettes being disposed about the carousel for receiving and mixing a reagent and a sample, each improved cuvette comprising a sample holding means being disposed in each cuvette for receiving the sample, the sample holding means being located radially outward from the center of the carousel and a chamber being disposed for receiving the reagent, the chamber being located below said sample holding means and radially inward of said sample holding means, the chamber further being disposed in the optical path so that radiant energy is passed therethrough, whereby rotation of the carousel at a first speed allows the radiant energy to pass through the reagent prior to mixing with the sample, and rotation at a second speed causes the reagent in each cuvette to flow towards the sample holding means to effect mixture of the reagent with the sample.

It is the object of this invention to provide an improved analytical photometer that is simple in structure and accurate in use.

Another object of this invention is to provide an analytical photometer that allows for objectively obtaining a zero reading of the reagent prior to mixture of reagent and sample.

Still another object of this invention is to provide for zero blank readings on each cuvette while the carousel is rotating thereby not mixing the reagents with the samples. This eliminates the need for cuvette-to-cuvette dependency as used in the art of spectrophotometric analysis.

Yet another object of this invention is to provide an improved chemical analysis photometer that allows the same chamber to be used as both a reagent chamber and a reaction/optical chamber.

It is still another object of this invention to provide a chemical analysis photometer system capable of performing analysis on a large number of discrete samples simultaneously, which allows for the use of the carousel of cuvettes to be used in a system with selectable wavelength capability thereby providing for the testing of uncommon substances within a single carousel.

A feature of this invention is a unique carousel design that accomplishes mixing by bringing the reagent to the sample repeatedly, thereby relieving the responsibility of total and complete transfer of material from one chamber to the other as shown in the prior art. An advantage of the present invention resides in the provision of a unique cuvette structure which is simple in operation while allowing for an accurate reagent blank reading prior to mixture and analysis.

Another advantage of this invention is that there is no need for cuvette-to-cuvette dependency (or for matched and precalibrated cuvettes) as in the prior art devices.

Still another advantage of this invention is the provision for spectrophotometric analysis by taking readings from only one cuvette without the need for reference to the remaining cuvettes. This eliminates the need for reference to a reagent blank cuvette.

Other objects, features and advantages of the present invention will become clear following a reading of the detailed description when taken in conjunction with the drawings.

BRIEF DESCRIPTION OF THE DRAWINGS

FIG. 1 is a cross-sectional view of the photometer of this invention;

FIG. 2 is a plan view of several unique cuvettes of this invention arranged in a carousel;

FIG. 3 is a detailed cross-sectional view of a single cuvette of this invention taken along the section line 3—3 of FIG. 2; and, FIG. 4 is a partial bottom-side view of selected ones of the cuvette reaction chambers arranged in the carousel which shows projections for use in synchronizing mechanical motion with concomitant electrical circuitry.

DETAILED DESCRIPTION

Referring now to the drawings, and in particular to FIG. 1, a cuvette 10 is shown in cross section diametrically opposed from a partial view of another cuvette 12, each of which being arranged in a carousel 13 of a multiplicity of such cuvettes disposed about a shaft 14. The cuvettes are supported by a carousel plate 16 supported by a flange 18 pressed onto the shaft 14 at 20. A collar 17 is provided for securing the carousel 13 to the shaft 14 by means of gripping members 15 that clamp to the shaft at shaft detents 14a. The shaft 14 is rotated by a motor 22 in a direction as illustrated by an arrow 24. A source of radiant energy (e.g. light) is supported in proximity to the carousel 13 of cuvettes 10, 12, etc. by means of a base plate 26. The radiant energy source includes, for example, a light source 28 directed towards a lens 30 concentric with an optical path 32. Opening 34 is provided in the base plate flange 26 to allow the light rays to pass through the lens 30 to a mirror 36. Mirror 36 redirects the light along a second optical path 38 towards a photomultiplier 40. An additional flange plate 42 is affixed to the base plate 26 for supporting the photomultiplier in the optical path 38. Openings 44 and 46 are provided in the flange plate 42 concentric with the optical path 38.

With reference to the cuvette 10, as being exemplary of a multiplicity of the cuvettes of the carousel 13 disposed radially about the axis 14, a shelf 50 is disposed on the outward side of the cuvette for receiving a sample under analysis. The sample placed on the sample holding means 50 (i.e. a shelf, platform or the like) may, for example, be a blood sample and would be in the range of about one to a hundred microliters in volume. A reagent selected to react with the sample for analysis purposes is placed in a reaction chamber 52, normally the volume of the reagent is in the range from about 0.3 Ml to about 0.70 Ml. The chamber 52 is disposed within the optical path 38 for effecting analysis of the mixture of the reagent and sample as will be described in greater detail hereinbelow.

The arrangement of the reagent chamber 52 in the optical path 38 allows for obtaining a reagent blank reading when such reading is necessary prior to mixing the reagent and sample. The terms "zero reading" or "reagent blank reading" as used herein refer to effecting a photometric analysis of the reagent before the reagent is mixed with a sample. It is thus not necessary for each cuvette to be matched to the other, as in the prior art, since a zero reading may be taken independently on each cuvette. This eliminates the need for reference to the remaining cuvettes, since the need for reference to a separate reagent blank cuvette is eliminated.

Either the reagent or the sample may be loaded into the cuvette by automatic loading or manually by a hand held pipette. The cuvette design of this invention may be incorporated into a system with selectable wavelength capability for simultaneously testing uncommon substances within a single carousel of cuvettes.

The preferred embodiment of my invention includes a lip flange 56 immediately adjacent to the sample shelf 50 which improves the operation of my invention, and allows for the deposit of a large sample on the shelf 50 than one could use without such lip 56. Typically wall 56 is about one-hundred thousandth of an inch (0.100 in.) in height. Each cuvette 10 also includes a sloping edge 58 directed radially outward to enhance mixture of the reagent with the sample, and provides for easy access to the shelf 50.

I have found that the incorporation of an additional chamber 60, which is located radially inward of the reaction chamber 52, allows for a secondary reagent or material to be mixed with the reagent or material in the optical path. This is convenient if one reagent is unstable when mixed with the other reagent, thereby precluding mixing reagents or reagents and sample prior to reading.

In operation, a reagent blank reading is normally obtained when the carousel 13 is rotating at approximately sixty (60) RPM's, that is at 60 RPM's the chamber 52 has sufficient reagent to obtain a zero reading. Upon further acceleration to one hundred and twenty (120) to four hundred (400) RPM's the reagent in the chamber 52 moves up wall 62 of the cuvette 10 to mix with a sample placed on the shelf 50. The carousel is then deaccelerated and again accelerated from 2 to 10 times to properly mix the reagent with the sample. Subsequently, after an appropriate time delay, as determined by the particular sample and reagent used, light from source 28 is passed through the chamber 52 to the photomultiplier 40 to thereby obtain a reading. The output of the photomultiplier 40 may be provided on an electrical lead 64 to an electronic analysis circuitry 65. Details of a typical electronic analysis circuitry 65, suitable for performing the analysis is well known in the art.

Referring now to FIG. 2, a plan view of a carousel 13 containing a multiplicity of cuvettes 10 is shown, wherein details of the chambers 50 and 52 may be seen. The chambers 60 are disposed radially inward from the chambers 50 and 52 to allow for mixing upon acceleration by centrifical force of a second or ancillary reagent when placed in this compartment 60. The chamber 60 is especially useful when initial mixture of a first and a second reagent can cause instability over time. Also, one could use the chamber 60 for holding a solid phase material, such as a catalyst or other material useful in the analysis.

Also, FIG. 2 shows details of the flange 16 containing the collar 17 in its relationship with the carousel 13. Further, the plan view of FIG. 2 illustrates wall 62 and the lip flange 56 in greater detail.

The cross-sectional view of FIG. 3 illustrates the cuvette 10 in greater detail. Like reference numerals are used in FIG. 3 to illustrate the same components or chambers of the cuvette 10 as described hereinabove. However, FIGS. 3 and 4 illustrate another embodiment of my invention useful for timing the mechanical rotation of the carousel 13 with the electrical analysis circuitry 65. More particularly, projection 72a is disposed on the chamber 52 for locating the wheel position or rotation by optical phasing, and the projections 72b provide mechanical balance. FIG. 4 shows a partial bottom-side view of selected ones of the cuvette reaction chambers 52 arranged in the carousel. Projection 72a in combination with a light source and photodetector produces a once-around signal for the circuitry 65. The three projections 72b are arranged at 90°, 180° and 270° (when projection 72a is at 0°) to stabilize rotation of the carousel assembly.

It is noted that projections 72a and 72b, or the like, may be disposed on selected cuvettes at various locations other than as shown in FIG. 4, and yet allow for a mechanical-to-electrical timing means.

While specific embodiments of my invention have been disclosed with particularity, it is understood that those skilled in the art will make numerous variations, changes and modifications thereof without departing from the scope of my invention. It is therefore intended that I be granted United States Letters Patent limited only by the invention as defined in the appended claims.

I claim:

1. In a photometric solution analyzer of the rotary type wherein a carousel includes a multiplicity of improved cuvettes, said carousel being journaled on a shaft driven by a motor, said analyzer further including means for permitting transfer of radiant energy from a source thereof to a detector therefor along an optical path passing through at least a part of each of said cuvettes, said cuvettes being disposed about said carousel for receiving and mixing a reagent and a sample, each improved cuvette comprising:

a sample holding means being disposed in each cuvette for receiving the sample, said means being located radially outward from the center of said carousel; and, a chamber being disposed for receiving the reagent, said chamber being located below said sample holding means and radially inward of said sample holding means, said chamber further being disposed in the optical path so that radiant energy is passed therethrough, whereby rotation of said carousel at a first speed allows the radiant energy to pass through the reagent prior to mixing with the sample, and rotation at a second speed causes the reagent in each cuvette to flow towards said sample holding means to effect mixture of the reagent with the sample for analysis.

2. An improved cuvette structure as defined in claim 1 further characterized by a second chamber being disposed above and radially inward of said chamber for receiving a second reagent.

3. An improved cuvette structure as defined in claim 1 further characterized by selected ones of said cuvettes, when arranged in a carousel of cuvettes, including mechanical-to-electrical timing means.

4. An improved cuvette structure as defined in claim 1 further characterized by said sample holding means including a lip extension disposed for increasing the sample holding means size.

5. An improved cuvette structure as defined in claim 1 further characterized by said carousel including a collar disposed for securing said carousel to said shaft.

6. An improved cuvette structure as defined in claim 1 further characterized by said first speed being about 60 RPM's.

7. An improved cuvette structure as defined in claim 1 further characterized by said second speed being about 120 to 400 RPM's.

* * * * *